US00PP08661P

United States Patent [19]

Bringhurst et al.

[11] Patent Number: Plant 8,661

[45] Date of Patent: Mar. 29, 1994

[54] STRAWBERRY PLANT CALLED SUNSET

[75] Inventors: Royce S. Bringhurst; Douglas V. Shaw, both of Davis; Victor Voth, Santa Ana, all of Calif.

[73] Assignee: The Regents of the University of California, Oakland, Calif.

[21] Appl. No.: 41,639

[22] Filed: Apr. 1, 1993

[51] Int. Cl.[5] ..... A01H 5/00

[52] U.S. Cl. ..... Plt./49

[58] Field of Search ..... Plt. 48, 49

*Primary Examiner*—James R. Feyrer

*Attorney, Agent, or Firm*—Townsend and Townsend Khourie and Crew

[57] ABSTRACT

'Sunset' is a day-neutral cultivar similar to 'Selva' (U.S. Plant Pat. No. 5,266) but with a consistently later pattern of production, larger fruit, better flavor and superior tolerance to two-spotted spidermite (*Tetranychus urticae*).

2 Drawing Sheets

DESCRIPTION

This invention relates to a new and distinctive day-neutral type cultivar designated as 'Sunset', which resulted from a cross performed in 1985 between advanced selection Cal 75.121-101 (the day-neutral parent of 'Capitola'; U.S. Plant Pat. No. 7,615) and Cal 81.16-604, a hybrid between Cal 71.98-605 (the firm parent of 'Parker'; U.S. Plant Pat. No. 5,263 and 'Selva'; U.S. Plant Pat. No. 5,266) and 'Chandler' (U.S. Plant Pat. No. 5,262).

'Sunset' was first fruited at the University of California Wolfskill Experimental Orchards near Davis, Calif. in 1986, where it was selected, originally designated Cal 85.22-1, and propagated asexually by runners. Asexual propagules from this original source have been tested at the Watsonville Strawberry Research Facility, University field stations, and to a limited extent in grower fields starting in 1987.

Figure 1:
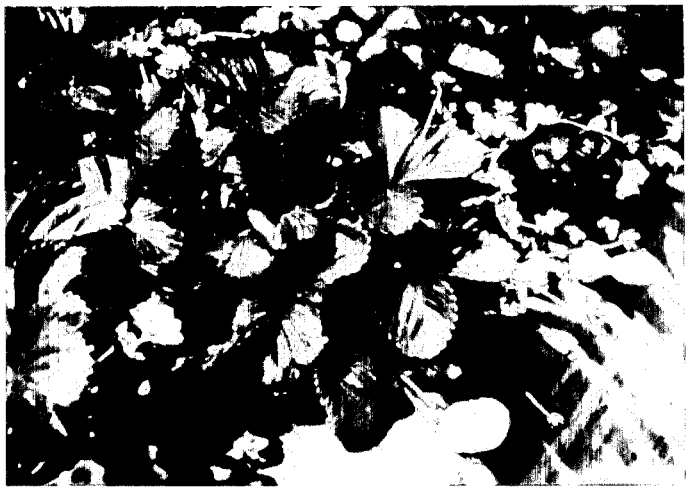
FIG. 1 shows the general flowering and fruiting characteristics of the plant.
Figure 2:
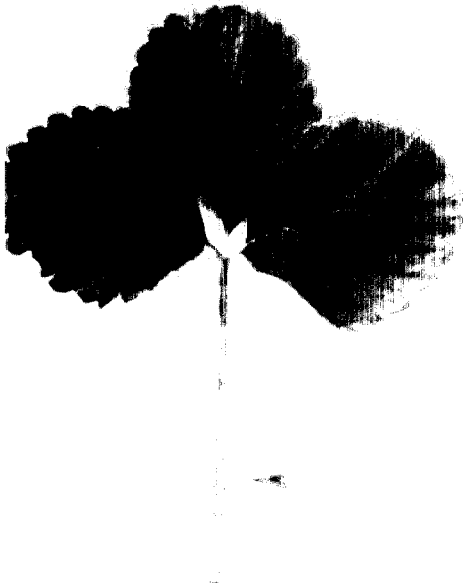
FIG. 2 shows a typical mature leaf during late spring.
Figure 3:
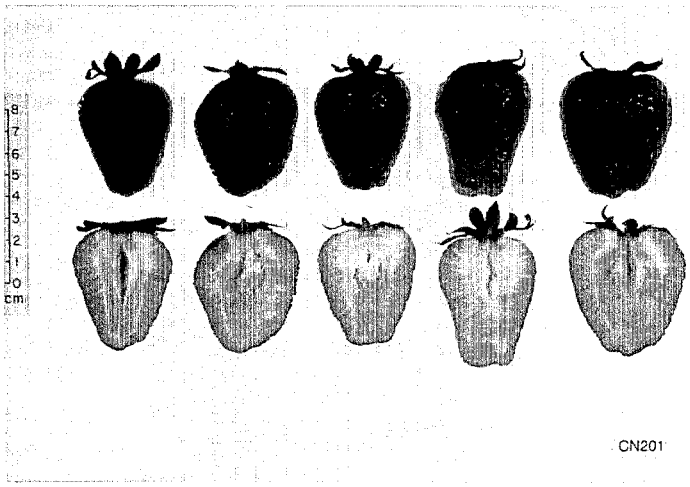
FIG. 3 shows representative mid-season fruit.

'Sunset' is moderate to weak in expressing the day-neutral character, being a stronger day-neutral than 'Seascape' (U.S. Plant Pat. No. 7,614), comparable or slightly more day-neutral than 'Selva', and less so than 'Fern' (U.S. Plant Pat. No. 5,267) or 'Irvine' (U.S. Plant Pat. No. 7,172). The production pattern for 'Sunset' is slightly later than for 'Selva' or 'Seascape', and will be of special interest for winter plantings, where 'Selva' has been successful.

Plants and foliage: Fruiting plants of 'Sunsset' are more erect and usually more vigorous than plants of 'Selva' or 'Seascape'. With appropriate treatment, 'Sunset' is a slightly larger plant than 'Selva', and similar in size to 'Seascape'. 'Sunset' forms branch crowns in similar quantity to 'Selva' with slightly less branching than 'Seascape'. When propagated in the nursery, 'Sunset' has similar runner production capacity to 'Selva'. Comparative statistics for foliar characters, including leaf color, near mid-season are given for the three cultivars in Table 1. Leaflets and leaves (including petioles) are somewhat larger and more narrow than leaves of 'Selva' or 'Seascape'. Also, leaves for 'Sunset' are somewhat lighter in color and more yellow than the comparison cultivars, with visual comparisons of leaf color to the Munsell color scale (Nickerson Color Fan) given in Table 5. Leaf color is distinctly lighter on the underside for 'Sunset', but the differential is not as large as for 'Selva' or 'Seascape'. 'Sunset' has very concave leaves compared with 'Selva' and 'Seascape'. Petioles for 'Sunset' are similar in thickness to those of 'Selva', and are less thick than those of 'Seascape'. Paired stipules, borne in a median position on the petiole, appear as small, stalked, ovate to heart-shaped structures on some leaves for 'Sunset' and on most leaves for the comparison cultivars. Stipule size varies greatly both within and among individual plants for 'Sunset', and one or both stipules are frequently absent or may be abscise as the leaf matures. Leaf and petiole pubescence characters for 'Sunset' are similar to those for 'Seascape'.

Isozymes in leaf extracts: 'Sunset' has been classified for three isozyme systems using starch gel electrophoresis (Table 2): Phosphoglucoisomerase (PGI), Leucine Aminopeptidase (LAP), and Phosphoglucomutase (PGM). It is distinguishable from all other day-neutral cultivars released to date except 'Mrak'. For electrophoretic procedures see: J. Amer. Soc. Hort. Sci. 106:684–687.

Disease and pest reaction: 'Sunset' is moderately susceptible to common leaf spot (*Ramularia tulasnei*) and highly susceptible to powdery mildew (*Sphaerotheca macularis*). When treated properly, it is less susceptible to two-spotted spidermites (*Tetranychus urticae*) than 'Selva', and is tolerant to strawberry viruses encountered in California.

TABLE 1

Foliar characteristics for 'Sunset', 'Selva', and 'Seascape'.

| Foliar Character | Cultivar 'Sunset' | 'Selva' | 'Seascape' |
|---|---|---|---|
| Mid-tier leaflet | | | |
| Length (mm) | | | |
| mean | 90.2 | 83.8 | 82.6 |
| range | 77–98 | 80–88 | 78–88 |
| Width (mm) | | | |
| mean | 67.0 | 66.4 | 71.2 |
| range | 65–68 | 62–75 | 67–75 |
| Mid-tier leaf | | | |
| Length (mm) | | | |
| mean | 234.0 | 209.8 | 208.8 |
| range | 204–269 | 187–238 | 180–230 |
| Width (mm) | | | |
| mean | 158.2 | 148.2 | 152.8 |

TABLE 1-continued

Foliar characteristics for 'Sunset', 'Selva', and 'Seascape'.

| Foliar Character | Cultivar 'Sunset' | 'Selva' | 'Seascape' |
|---|---|---|---|
| range | 140–172 | 135–163 | 137–177 |
| Leaf color (CIELAB)* | | | |
| L* | | | |
| mean | 29.9 | 31.3 | 28.1 |
| range | 28.0–32.2 | 29.5–32.9 | 25.9–30.5 |
| a* | | | |
| mean | −7.7 | −6.7 | −5.4 |
| range | −7.0–−9.1 | −4.8–−8.9 | −4.1–−7.2 |
| b* | | | |
| mean | 17.0 | 15.3 | 10.5 |
| range | 13.5–21.0 | 12.5–19.4 | 9.3–11.1 |
| # leaflets/leaf | 3 | 3 | 3–4 |
| Leaf convexity | concave | flat/convex | flat/slight convex |
| Serrations | | | |
| number | many | moderate/few | moderate |
| shape | semi-pointed to pointed | semi-pointed to pointed | semi-round |
| Leaf pubescence | moderate | heavy | moderate |
| Petiole pubescence | | | |
| density | moderate | heavy | heavy |
| direction | perpendicular | slightly acropetal | perpendicular |

*CIELAB is the abbreviation of the international color system known as "Commission Internationale De L'Eclairage" 1978. Recommendations on uniform color spaces — color difference equations, psychometric color terms, Supplement No. 2 to CIE Publication No. 15. PARIS.

TABLE 2

Isozyme phenotypes for 'Sunset', 'Selva', and 'Oso Grande'.

| Locus | Cultivar 'Sunset' | 'Selva' | 'Seascape' |
|---|---|---|---|
| PGI | A1 | A2 | A4 |
| LAP | B3 | B3 | B3 |
| PGM | C2 | C2 | C2 |

Flowering, fruiting, fruit, and production characteristics: 'Sunset'is similar to other California day-neutral cultivars (e.g. 'Selva' and 'Seascape') in that it will flower independently of day length, given appropriate temperature and fertility conditions. Comparative statistics for flower and fruit characters, including fruit color, near mid-season are given for the three cultivars in Table 3, and visual comparisons of fruit color according to the Munsell color scale (Nickerson Color Fan) are given in Table 5. The flowers and sepals on primary fruit for 'Sunset' are somewhat smaller, and each flower tends to have more petals than for the comparison cultivars. The calyx on primary fruit for 'Sunset' is usually slightly indented into the fruit shoulder. The fruit shape for 'Sunset' is a flat conic, sometimes heart-shaped, and is easily distinguished from other California day-neutral cultivars. Fruit color for 'Sunset' is similar to that for 'Selva', both internal and external, but the fruit is much more glossy. Achenes vary from yellow to light red, and are slightly indented.

'Sunset' has been tested under a variety of cultural regimes, and optimal performance is obtained when nursery treatments, pre-plant chilling regimes, plant densities, and nutritional programs similar to those that optimize performance for 'Selva' are used.

When treated with appropriate planting regimes, 'Sunset' has larger fruit and produces greater yields than 'Selva' or 'Seascape' (see graph and table 4). Commercial appearance ratings have been comparable to those for 'Selva'. Fruit firmness is similar to that for 'Seascape'. Subjectively, 'Sunset' has very good flavor, substantially better than 'Selva', but probably not equal to that for 'Seascape'. The fruit will be acceptable for fresh market, and home garden purposes. Fruit from 'Sunset' also has firmness (character) and internal color acceptable for processing.

TABLE 3

Flower and fruit characters for 'Sunset', 'Selva', and 'Seascape'.

| Character | Cultivar 'Sunset' | 'Selva' | 'Seascape' |
|---|---|---|---|
| # petals | | | |
| mean | 6.0 | 5.6 | 5.2 |
| range | 5–7 | 5–6 | 5–6 |
| Flower position (relative to foliage) | even/ exposed | even/ internal | even/ exposed |
| Calyx diam. (mm) | | | |
| mean | 36.1 | 39.1 | 41.0 |
| range | 30–41 | 34–44 | 35–47 |
| Corolla diam. (mm) | | | |
| mean | 27.7 | 38.5 | 38.7 |
| range | 25–35 | 33–41 | 35–41 |
| Fruit shape | | | |
| length/width ratio | 1.18 | 1.20 | 1.19 |
| subjective | flat conic | ovate conic | conic |
| Calyx position | even/ indented | slight indent | slight neck |
| Seed position | slight indent | even/slight indent | slight extrude |
| Fruit color (CIELAB) | | | |
| external | | | |
| L* | 24.4 | 25.4 | 22.8 |
| a* | 31.8 | 31.7 | 29.8 |
| b* | 16.9 | 16.8 | 15.1 |
| internal | | | |
| L* | 46.7 | 45.6 | 46.0 |
| a* | 37.7 | 36.3 | 40.2 |
| b* | 30.3 | 27.7 | 31.6 |

TABLE 4

Performance for selection 'Sunset' compared with 'Seascape' and 'Selva' at the Watsonville Research Facility for the 1991 trial and the average of 1989, 1990 and 1991 trials. All plants were dug from the South Coast nursery near MacDoel, CA in mid-October, and planted after four weeks storage.

| Item | Test Year(s) | Yield (g/plant) | Size (g/fruit) | Appearance Score | Firmness |
|---|---|---|---|---|---|
| 'Sunset' | 1991 | 2,226 | 28.8 | 3.9 | 7.8 |
| | 1989, 90, 91 | 2,283 | 29.2 | 3.6 | 6.8 |
| 'Seascape' | 1991 | 2,030 | 25.3 | 3.9 | 7.8 |
| | 1989, 90, 91 | 1,998 | 25.9 | 4.0 | 7.0 |
| 'Selva' | 1991 | 1,962 | 24.1 | 3.5 | 8.1 |
| | 1989, 90, 91 | 1,928 | 24.7 | 3.4 | 7.7 |

TABLE 5

Munsell color classification for leaf and fruit characters.

| Item | Munsell Leaf Color Classes: Upper (Adaxial) | Lower (Abaxial) | Munsell Fruit Color Classes: External | Internal |
|---|---|---|---|---|
| Selva | 10GY 5/8 | 5G 7/8 | 5R 4/12 | 7.5R 6/12 |
| | 2.5G 5/9 | | 5R 6/11 | |
| Seascape | 7.5GY 4/4 | 7.5G 6/8 | 5R 3/7 | 7.5R 5/13 |
| | 10GY 4/5 | 7.5G 5/8 | 2R 3/7 | 7.5R 4/11 |
| Sunset | 5GY 5/6 | 5G 6/8 | 5R 4/12 | 7.5R 5/13 |
| | | 5G 7/8 | 7.5R 4/11 | |

We claim:

1. The new and distinct variety of strawberry plant illustrated and described and having the characteristics above enumerated.

* * * * *